United States Patent
Ma et al.

(10) Patent No.: US 11,026,988 B2
(45) Date of Patent: Jun. 8, 2021

(54) TRADITIONAL CHINESE MEDICINE COMPOSITION AND USE THEREOF

(71) Applicant: INFINITUS (CHINA) COMPANY LTD., Guangdong (CN)

(72) Inventors: Fangli Ma, Guangdong (CN); Yuanyuan Wang, Guangdong (CN); Minghua Hu, Guangdong (CN); Renhuai Cong, Guangdong (CN); Lingyun Xiao, Guangdong (CN); Chung Wah Ma, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 219 days.

(21) Appl. No.: 16/058,484

(22) Filed: Aug. 8, 2018

(65) Prior Publication Data

US 2019/0070246 A1    Mar. 7, 2019

(30) Foreign Application Priority Data

Sep. 7, 2017 (CN) .......................... 201710799353.6

(51) Int. Cl.
| | | |
|---|---|---|
| *A61K 36/54* | (2006.01) | |
| *A61K 36/00* | (2006.01) | |
| *A61K 36/815* | (2006.01) | |
| *A23L 33/105* | (2016.01) | |
| *A23L 33/115* | (2016.01) | |
| *A23L 33/12* | (2016.01) | |
| *A23L 33/125* | (2016.01) | |
| *A61P 35/00* | (2006.01) | |
| *A61K 31/715* | (2006.01) | |
| *A61K 36/61* | (2006.01) | |
| *A61K 36/8969* | (2006.01) | |

(52) U.S. Cl.
CPC .......... *A61K 36/815* (2013.01); *A23L 33/105* (2016.08); *A23L 33/115* (2016.08); *A23L 33/12* (2016.08); *A23L 33/125* (2016.08); *A61K 31/715* (2013.01); *A61K 36/54* (2013.01); *A61K 36/61* (2013.01); *A61K 36/8969* (2013.01); *A61P 35/00* (2018.01); *A23V 2002/00* (2013.01); *A61K 2236/15* (2013.01); *A61K 2236/331* (2013.01); *A61K 2236/37* (2013.01); *A61K 2236/39* (2013.01); *A61K 2236/51* (2013.01); *A61K 2236/53* (2013.01); *A61K 2236/55* (2013.01)

(58) Field of Classification Search
None
See application file for complete search history.

(56) References Cited

U.S. PATENT DOCUMENTS

| 7,879,823 B2 * | 2/2011 | Seiberg | A61K 36/48 514/59 |
|---|---|---|---|
| 2011/0280911 A1 * | 11/2011 | Myc | A61K 39/39 424/277.1 |
| 2019/0314436 A1 * | 10/2019 | Hwang | A61K 36/84 |

FOREIGN PATENT DOCUMENTS

CN    106619695 A    5/2017

OTHER PUBLICATIONS

First Office Action dated Mar. 4, 2020 for Chinese patent application No. 201710799353.6, English translation provided by Global Dossier.
Cai Junlong et al., Analysis on Volatile Components of Caryophylli Flos from Different Habitats, Plant Science Journal, 2015, 33(2), 251-258.
Wu Cunen, Research Progress on Active Components and Antitumor Effects of Cinnamomum cassia, Lishizhen Medicine and Materia Research, 2015 vol. 26 No. 8.

* cited by examiner

*Primary Examiner* — Michael Barker
*Assistant Examiner* — Randall O Winston
(74) *Attorney, Agent, or Firm* — Yue (Robert) Xu; Apex Attorneys at Law, LLP

(57) ABSTRACT

The present disclosure relates to the field of drugs and health foods. Disclosed is a traditional Chinese medicine composition comprising *Lycii fructus* polysaccharide, *Polygonati rhizoma* polysaccharide, *Caryophylli flos* oil and *Cinnamomi cortex* oil. Experiments show that the traditional Chinese medicine composition has a scientific formulation, synergistic functions, without toxic and side effects, and not only has nutritional value but also inhibits the growth of tumor. Comparing with individual components, the composition significantly increases the percentages of $CD4^+$ and $CD8^+$ cells in lymphocytes of the tumor stroma, increases body immune function, recovers normal immune surveillance function, decreases the expression rate of VEGF and TGF-β 1 positive cells in tumor tissue, assists in treating tumor, increases antitumor effects of chemotherapy drugs, improves immune status of body, has the function of restoring normal immune surveillance, preventing and assisting in treating tumor.

5 Claims, No Drawings

TRADITIONAL CHINESE MEDICINE COMPOSITION AND USE THEREOF

CROSS REFERENCE TO RELATED APPLICATIONS

This application claims the priority of Chinese Patent Application No. 201710799353.6, filed on Sep. 7, 2017, and the disclosures of which are hereby incorporated by reference.

FIELD

The present disclosure relates to the field of drugs and health foods, specifically to a traditional Chinese medicine composition and use thereof, in particular to a traditional Chinese medicine composition that contains various vegetable polysaccharides and vegetable oils, and use thereof.

BACKGROUND

Tumor is a new organism formed by the proliferation of local tissue cells under the action of various tumorigenic factors. According to the hazard of the tumors to the human body and their growth characteristics, tumors are divided into two types: benign tumors and malignant tumors. Benign tumors, for example lipoma, hemangioma, adenoma, cysts and so on, grow slowly, showing an expansive growth, which have intact pseudocapsule over their surface. There is seldom systemic symptom except for local symptoms. Benign tumors do not infiltrate into surrounding tissues or metastasize to the whole body, and are not easy to relapse after surgical resection, and are less harmful to the body. Malignant tumors, for example bone cancer, esophageal cancer, liver cancer, lung cancer, leukemia, osteosarcoma and so on, grow rapidly, often infiltrate into the surrounding tissues and metastasize to the whole body. There is almost no pseudocapsule over the surface of malignant tumors. Pathological examination shows atypical karyokinesis mitoses. Except for local symptoms, systemic symptoms are obvious. Patients in the late stage often have cachexia, and have a high relapse rate after surgical resection, which are greatly harmful to the body. Tumor is currently at the top of the cause of death spectrum and it is a major health threat.

The main traditional methods for treating malignant tumors include surgery, radiation therapy and chemotherapy. Surgical treatment is the most important way to treat malignant tumors, especially for early- and mid-stage malignant tumors, which is listed as the preferred method. After surgical resection, some early-stage tumors can be completely cured, and the patients can survive for a long time. Radiation therapy (radiotherapy) uses radiation to induce changes of DNA, chromosomal aberration or break in tissue cells, and ionization of cellular fluid to generate chemical free radicals, finally leading to deactivation of cells or their filial generation, so as to break the cells or inhibit the growth of tumor. Radiation has adverse effects on normal tissue cells, especially with the increasing amount of light radiation, it easily damages hematopoietic organs and vascular tissues, and causes leukopenia, thrombocytopenia, changes in skin and mucous membranes, gastrointestinal reactions and so on. Chemical drug therapy (chemotherapy) is also known as anticancer drug treatment. It is mainly applicable to the comprehensive therapy of mid- and late-stage cancer. Clinically, chemotherapy has a good effect on chorionic epithelioma, acute lymphoblastic leukemia, malignant lymphoma and so on. For other malignant tumors, chemotherapy can assist surgery or radiotherapy. However, all of the above three conventional treatment methods have certain limitations and cause certain painful feelings to the patients, especially radiotherapy and chemotherapy have inhibition effects on the normal immune system in some degree.

With the development of tumor immunology, people are increasingly aware that the immune system is critical for the surveillance and clearance of tumors. Immunotherapy is regarded as the fourth type of therapy that is expected to overcome cancer. In the past, people concerned about positive immunity, that is, the direct killing of tumor cells by immune cells. However, at present, the academic community believes that the immune negative regulation cells have become new targets for treating cancer. Immune escape of tumor cells is an important prerequisite for the development of tumors. The reason why this important biological event occurs is that there is an immune negative regulation network in the tumor microenvironment, and the immune negative regulatory cells and factors in this network inhibit the surveillance and clearance of tumor cells by immune effector cells.

SUMMARY

An object of the present disclosure is to provide a traditional Chinese medicine composition having the function of improving tumor microenvironment, a method for preparing the same, and use thereof.

In order to achieve the goal of the present disclosure, the following technical solutions are used in the present disclosure.

A traditional Chinese medicine composition, which comprises *Lycii fructus* polysaccharide, *Polygonati rhizoma* polysaccharide, *Caryophylli flos* oil and *Cinnamomi cortex* oil.

Preferably, in the tradition Chinese medicine composition, the weight ratio of *Lycii fructus* polysaccharide, *Polygonati rhizoma* polysaccharide, *Caryophylli flos* oil and *Cinnamomi cortex* oil is (1 to 5):(1 to 5):(1 to 5):(1 to 5).

More preferably, in the tradition Chinese medicine composition, the weight ratio of *Lycii fructus* polysaccharide, *Polygonati rhizoma* polysaccharide, *Caryophylli flos* oil and *Cinnamomi cortex* oil is (1 to 2):(1 to 2):(1 to 2):(1 to 2).

In some embodiments of the present disclosure, in the tradition Chinese medicine composition, the weight ratio of *Lycii fructus* polysaccharide, *Polygonati rhizoma* polysaccharide, *Caryophylli flos* oil and *Cinnamomi cortex* oil is 1:1:1.5:1.5.

In the traditional Chinese medicine composition of the present disclosure, *Lycii fructus* polysaccharide, *Polygonati rhizoma* polysaccharide, *Caryophylli flos* oil and *Cinnamomi cortex* oil are either extracted from plants or artificially synthesized.

In the traditional Chinese medicine composition of the present disclosure, the method for preparing *Lycii fructus* polysaccharide, or *Polygonati rhizoma* polysaccharide is: respectively pulverizing the *Lycii fructus* or *Polygonati rhizoma*, mixing the *Polygonati rhizoma* or *Polygonati rhizoma* fine powders with water in a weight ratio of 1:(2.5 to 10), heating and stirring for extraction for 2 to 4 hours at temperature between 70 and 75° C., collecting the filter residue, extracting the residue for twice according to the solid-to-liquid ratio, temperature and duration above, combining the extracts of the three times, concentrating under reduced pressure and centrifuging to give a clarified concentrate, mixing the clarified concentrate with alcohol of 95% (v/v) in a volume ratio of 1:(7 to 10), holding and precipitating at 4° C., centrifuging and collecting the precipitation, vacuum freeze-drying, and respectively obtaining the *Lycii fructus* polysaccharide or *Polygonati rhizoma* polysaccharide.

In the traditional Chinese medicine composition of the present disclosure, the method for preparing the *Caryophylli flos* oil is: mixing the *Caryophylli flos* fine powder with water which is 15 times the weight of the *Caryophylli flos* fine powder, soaking for 1 hour, subjecting to steam distillation extraction and extracting for 4 to 5 hours at temperature between 130 and 140° C. and with a vapor flux of 2 L/h. The *Caryophylli flos* fine powder is preferably 40-mesh filtered *Caryophylli flos* fine powder. The *Caryophylli flos* oil obtained is colorless and transparent, with a spicy fragrance of bryophyte and costustoot, and a yield from 8 to 10%, which is preserved in a refrigerator at −20° C.

In the traditional Chinese medicine composition of the present disclosure, the method for preparing the *Cinnamomi cortex* oil is: adding water which is 3 times the weight of the *Cinnamomi cortex* fine powder to the *Cinnamomi cortex* fine powder and mixing, soaking for 3 hours, subjecting to steam distillation, and extracting for 4 hours at temperature between 120 and 140° C. and with a vapor flux of 2 L/h. The *Cinnamomi cortex* fine powder is preferably 40-mesh filtered *Cinnamomi cortex* fine powder. The *Cinnamomi cortex* oil obtained has a yellowish-brawn color, with a rich fragrance, and a yield from 2 to 3%, which is preserved in a refrigerator at −20° C.

The traditional Chinese medicine composition of the present disclosure is produced by mixing *Lycii fructus* polysaccharide, *Polygonati rhizoma* polysaccharide, *Caryophylli flos* oil and *Cinnamomi cortex* oil.

It is surprisingly found through experiments that the components of the composition of the present invention has a scientific formulation, which shows significantly superior effects than individual components of the traditional Chinese medicine composition, and the effects are unexpected by one of ordinary skill in the art. Cytological experiments show that comparing with individual component of the traditional Chinese medicine composition, the traditional Chinese medicine composition of the present disclosure significantly inhibits tumor growth, increases the percentage of CD4$^+$ and CD8$^+$ cells in tumor interstitial lymphocytes, and decreases the expression rate of VEGF and TGF-β 1 positive cells in tumor tissue, so as to restore normal immune function for tumor surveillance, prevent immune escape of tumor cells, enhance the anti-tumor effect of chemotherapeutic drugs, therefore playing a role of preventing and/or assisting in treating tumor.

Thus, the present disclosure provides use of the traditional Chinese medicine composition in preparing health foods and/or drugs for inhibiting tumor growth.

The present disclosure further provides use of the traditional Chinese medicine composition in preparing health foods and/or drugs for increasing the percentage of CD4$^+$ and CD8$^+$ cells in lymphocytes of tumor stroma.

The present disclosure further provides use of the traditional Chinese medicine composition in preparing health foods and/or drugs for decreasing the expression rate of VEGF and TGF-β1 positive cell in tumor tissue.

The present disclosure further provides use of the traditional Chinese medicine composition in preparing health foods and/or drugs for increasing immunity function.

The present disclosure further provides use of the traditional Chinese medicine composition in preparing health foods and/or drugs for restoring normal immune surveillance function.

Restoring normal immune surveillance function of the body includes inhibiting the growth of tumor, increasing percentage of CD4$^+$, CD8$^+$ cells in lymphocytes of tumor stroma, decreasing expression rate of VEGF and TGF-β1 positive cells in tumor tissue, assisting in treating tumor and improving immune status of the body.

The present disclosure further provides use of the traditional Chinese medicine in preparing health foods and/or drugs for preventing and/or assisting in treating tumor.

The present disclosure further provides drugs and/or health foods for improving immune function and preventing and/or assisting in treating tumor, which comprise the traditional Chinese medicine composition, and/or the traditional Chinese medicine composition obtained by the method of the present disclosure and a pharmaceutically acceptable excipient or a food acceptable excipient.

The pharmaceutically acceptable excipient or the food acceptable excipient includes carrier, adjuvant and/or filler, etc.

In some embodiments of the present disclosure, dosage forms of the drugs or the health foods are capsule, tablet, granule, oral liquid, powder, tea bag and other dosage forms of drugs or health foods.

It can be concluded from the technical solutions above that the present disclosure provides a traditional Chinese medicine composition, which comprises *Lycii fructus* polysaccharide, *Polygonati rhizoma* polysaccharide, *Caryophylli flos* oil and *Cinnamomi cortex* oil. Experiments show that the traditional Chinese medicine composition has a scientific formulation and each component works well with each other. The composition has no toxic and side effects, which not only has nutritional value but also inhibits the growth of tumor. Comparing with individual components, polysaccharide composition, oil composition, and compositions that lack at least one component, the traditional Chinese medicine composition significantly increases the percentage of CD4$^+$ and CD8$^+$ cells in lymphocytes of the tumor stroma, increases body immune function, recovers normal immune surveillance function, decreases the expression rate of VEGF and TGF-β 1 positive cells in tumor tissue, assists in treating tumor, increases antitumor effects of chemotherapy drugs, improves immune status of body, has the function of restoring normal immune surveillance, and has functions on preventing and assisting in treating tumors.

DETAILED DESCRIPTION

The present disclosure provides a traditional Chinese medicine composition and the application thereof. One of ordinary skill in the art can learn from the contents herein and improve the process parameters appropriately. In particular, it shall be noted that all the similar substitutions and modifications are apparent to one of ordinary skill in the art and are to be considered within the scope of the present invention. The method and product of the present invention have been described with preferred examples. It is apparent that one of the ordinary skill in the art can make change or modify the combination to the method and product of the present invention without departing from the spirit, scope and spirit of the invention, therefore realizing and applying the techniques of the present invention.

In order to understand the present disclosure further, the technical solutions in the embodiments of the present disclosure will be described clearly and completely herein in conjunction with Examples of the present disclosure. Apparently, the described examples are only a part of Examples of the present disclosure, rather than all examples. Based on Examples in the present disclosure, all of other examples, made by one of ordinary skill in the art without any creative efforts, fall into the protection scope of the present disclosure.

Without special illustration, all the reagents in Examples of the present disclosure are commercial products, which can be purchased on the market.

Example 1 Preparation of *Lycii fructus* Polysaccharide

*Lycii fructus* polysaccharide of the present disclosure was prepared by the following method. *Lycii fructus* was pulverized, and water was added at a weight ratio of *Lycii fructus*:water=1:10. Extraction was performed for 2 hours under conditions of heating and stirring at 70° C. The filter residue was collected and continuously subjected to extraction for twice according to the solid-to-liquid ratio, temperature and duration above. Extracts of the three extractions were combined, concentrated under reduced pressure and centrifuged to obtain a clarified concentrate. 95% alcohol which was 7 times the volume of the concentrate was added to the clarified concentrate, mixed, and the mixture was held for precipitation over night at 4° C. The mixture was centrifuged to collect the precipitates, and the precipitates were subjected to vacuum freeze-drying to obtain the *Lycii fructus* polysaccharide.

Example 2 Preparation of *Polygonati rhizoma* Polysaccharide

*Polygonati rhizoma* polysaccharide of the present disclosure was prepared by the following method. *Polygonati rhizoma* was pulverized, and water was added at a weight ratio of *Polygonati rhizoma*:water=1:5. Extraction was performed for 3 hours under conditions of heating and stirring at 75° C. The filter residue was collected and continuously subjected to extraction for twice according to the solid-to-liquid ratio, temperature and duration above. Extracts of the three extractions were combined, concentrated under reduced pressure and centrifuged to obtain a clarified concentrate. 95% alcohol which was 9 times the volume of the concentrate was added to the clarified concentrate, mixed, and the mixture was held for precipitation over night at 4° C. The mixture was centrifuged to collect the precipitates, and the precipitates were subjected to vacuum freeze-drying to obtain the *Polygonati rhizoma* polysaccharide.

Example 3 Preparation of *Caryophylli flos* Oil

*Caryophylli flos* oil of the present disclosure was prepared by the following method. 400 g of *Caryophylli flos* fine powder (40 meshes) was weighted, and water which was 15 times the weight of the fine powder was added and mixed to reach a solid-to-liquid ratio of 1:15. The fine powder was soaked for 1 hour and then subjected to steam distillation extraction. The extraction temperature was from 130 to 140° C., the vapor flux was 2 L/h, and the duration was 4 to 5 hours. The *Caryophylli flos* oil obtained is colorless and transparent, with a spicy fragrance of bryophyte and costustoot, and a yield from 8 to 10%, which is preserved in a refrigerator at −20° C.

Example 4 Preparation of *Cinnamomi cortex* Oil

*Cinnamomi cortex* oil of the present disclosure was prepared by the following method. 400 g of *Cinnamomi cortex* fine powder (40 meshes) was weighted, and water which was 3 times the weight of the fine powder was added and mixed to reach a solid-to-liquid ratio of 1:3. The fine powder was soaked for 3 hours and then subjected to steam distillation extraction. The extraction temperature was from 120 to 140° C., the vapor flux was 2 L/h, and the duration was 4 hours. The *Cinnamomi cortex* oil obtained has a yellowish-brawn color, with a rich fragrance, and a yield from 2 to 3%, which is preserved in a refrigerator at −20° C.

Example 5 Preparation of the Traditional Chinese Medicine Composition

*Lycii fructus* polysaccharide prepared in Example 1, *Polygonati rhizoma* polysaccharide prepared in Example 2, *Caryophylli flos* oil prepared in Example 3 and *Cinnamomi cortex* oil prepared in Example 4 were mixed at a weight ratio of 1:1:1.5:1.5 to obtain a traditional Chinese medicine composition comprising *Lycii fructus* polysaccharide, *Polygonati rhizoma* polysaccharide, *Caryophylli flos* oil and *Cinnamomi cortex* oil.

Example 6 Preparation of the Traditional Chinese Medicine Composition

*Lycii fructus* polysaccharide prepared in Example 1, *Polygonati rhizoma* polysaccharide prepared in Example 2, *Caryophylli flos* oil prepared in Example 3 and *Cinnamomi cortex* oil prepared in Example 4 were mixed at a weight ratio of 1:5:4:2 to obtain a traditional Chinese medicine composition comprising *Lycii fructus* polysaccharide, *Polygonati rhizoma* polysaccharide, *Caryophylli flos* oil and *Cinnamomi cortex* oil.

Example 7 Preparation of the Traditional Chinese Medicine Composition

*Lycii fructus* polysaccharide prepared in Example 1, *Polygonati rhizoma* polysaccharide prepared in Example 2, *Caryophylli flos* oil prepared in Example 3 and *Cinnamomi cortex* oil prepared in Example 4 were mixed at a weight ratio of 5:1:1:5 to obtain a traditional Chinese medicine composition comprising *Lycii fructus* polysaccharide, *Polygonati rhizoma* polysaccharide, *Caryophylli flos* oil and *Cinnamomi cortex* oil.

Example 8 Preparation of the Traditional Chinese Medicine Composition

*Lycii fructus* polysaccharide prepared in Example 1, *Polygonati rhizoma* polysaccharide prepared in Example 2, *Caryophylli flos* oil prepared in Example 3 and *Cinnamomi cortex* oil prepared in Example 4 were mixed at a weight ratio of 1:2:1:2 to obtain a traditional Chinese medicine composition comprising *Lycii fructus* polysaccharide, *Polygonati rhizoma* polysaccharide, *Caryophylli flos* oil and *Cinnamomi cortex* oil.

Example 9 Test the Function of the Traditional Chinese Medicine Composition on Preventing or Assisting in Treating Tumor

*Lycii fructus* polysaccharide, *Polygonati rhizoma* polysaccharide, *Caryophylli flos* oil, *Cinnamomi cortex* oil and the traditional Chinese medicine compositions obtained in examples 1 to 8 above were subjected to cell experiments by the inventors. The experiments were shown hereinafter.

1. Experiment Materials
1.1 Experiment Equipment and Reagents
  Flow cytometer: BD, Calibo.
  Analytical balance: Beijing Sartorius Co., Ltd., Sartorius BS124S type.
  Electronic balance: Beijing Sartorius Co., Ltd., Sartorius BL1500 type.

Carbon dioxide constant-temperature cell incubator (Nuaire).

Low-temperature high-speed centrifuge (Hunan Xingke TGL-16G).

The CD4$^+$, CD8$^+$ and antibody for flow cytometry were purchased from BD.

Lymphocyte separation solution (Guanzhou Zhanchen Biological Technology Co., Ltd.; China)

Fluorescein isothiocyanate labeled anti-mouse CD4 and CD8a monoclonal antibody (BioLegend, Inc., U.S.A.)

VEGF and TGF-β1 immunocytochemistry kit (Beijing Zhongshan Biological Technology Co., Ltd., China)

1.2 Experimental Drugs

The *Lycii fructus* polysaccharide, *Polygonati rhizoma* polysaccharide, *Caryophylli flos* oil and *Cinnamomi cortex* oil and the traditional Chinese medicine compositions prepared in examples 1 to 8, store at 4° C. and avoid light.

1.3 Experimental Animals

Female SPF mice were purchased from Laboratory Animal Research Center, Institute of Biophysics, Chinese Academy of Sciences. The mice were housed under conditions of 4 mice/box, temperature 20 to 25° C., RH 40 to 70% and 12 h:12 h day-night intermittently illumination. The mice have free access to food and drinking water, and the drinking water was distilled water prepared by the Laboratory Animal Research Center. The mice were divided into normal group, model group and groups of examples 1 to 8, 8 mice per group.

2. Experimental Method 2.1 Test of Inhibition Rate of Tumor

Colon cancer cell line CT26 was subcutaneously inoculated to Balb/c mice at an inoculation dosage of 1×10$^6$/mouse. 12 days later, the mice were administered by intragastric gavage with the compositions of examples 1 to 8. The administration was performed once a day at a dosage of 500 mg/kg/day. The normal group and the model group were administered by intragastric gavage with distilled water. On the 33$^{rd}$ day, 24 hours after the last administration, blood samples were collected from the hearts and the mice were sacrificed by cervical dislocation. The entire tumors were peeled off and weighed, and the inhibition rate of tumor was calculated.

The inhibition rate=(mean tumor weight of the model group−mean tumor weight of the administration group)/mean tumor weight of the model group×100%.

2.2 Test of CD4$^+$ and CD8$^+$ in Lymphocytes of Tumor Stroma and Intervention of the Traditional Chinese Medicine Composition Tumors were taken from the mice by surgery under asepsis condition. The tumors were weighted by an analytical balance and the tumors with a weight over 2 g were selected. A 1 mm$^3$ block was constructed from the selected tumor tissues, disposed in a RPMI-1640 culture medium containing 0.05% of collagenase, 0.02% of DNase, 0.01% of hyaluronidase and 10% of calf serum, and subjected to digestion under magnetic stirring at 4° C. overnight. The tissues were screened with a 200 meshes steel sieve. All the single cells were collected, subjected to low speed centrifugation (1500 r/min) for 15 minutes, and washed with Hanks solution for twice. The cell concentration was adjusted to about 1×10$^6$ cells/mL, i.e., tumor infiltrating lymphocyte.

2 EP tubes were prepared for each test sample. 50 µL cell suspension was added to each tube and the total volume was adjusted to 100 µL with a PBS buffer to reach a final concentration of 5×10$^5$ cells/mL. In one tube, 0.25 µg of anti-mouse CD4 monoclonal antibody and 0.2 µg of anti-mouse CD8a monoclonal antibody labeled with different fluorescein were added, and the other tube was set as the blank control tube. The tubes were incubated at room temperature for 30 minutes by avoiding light. The cells were washed with PBS and tested by a flow cytometer.

2.3 Test of Expression Rate of VEGF and TGF-β1 Positive Cells in Tumor Tissue

Immunohistochemistry methods were used according to the protocols. The results were determined by the appearance of brown color in cytoplasm of the VEGF and TGF-β 1 staining positive cells.

2.4 Statistical Method

All the experimental data in the experiments was statistically analyzed with software SPSS19.0. All the measurement data was expressed in the form of mean±standard deviation (−x±s), and t Test was performed. And the enumeration data was tested with $\chi^2$ Test. When P<0.05, the difference is statistically significant.

3. Experimental Results 3.1 Tumor Inhibition Rate in Mice

TABLE 1

Inhibition effect of the samples on tumor growth in mice (n = 8)

| Group | Normal Group | Model Group | Example 1 | Example 2 | Example 3 |
|---|---|---|---|---|---|
| Tumor Inhibition Rate (%) | — | — | 32.21 | 34.12 | 32.79 |

| Group | Example 4 | Example 5 | Example 6 | Example 7 | Example 8 |
|---|---|---|---|---|---|
| Tumor Inhibition Rate (%) | 33.45 | 45.37 | 39.78 | 39.89 | 43.11 |

As shown in Table 1, all the groups of examples 1 to 8 have inhibition effects on the growth of mice tumor. Therein, inhibition rate of Example 5 was the highest, 45.37%; the second was Example 8, 43.11%; while Example 1 has the least inhibition rate, 32.21%. The results indicated that both the individual components and the traditional Chinese medicine compositions were capable to inhibit the growth of tumor and played a role in preventing and assisting in treating tumor. However, the effects of the traditional Chinese medicine compositions were better than that of the individual components.

3.2 Effects on CD4$^+$, CD8$^+$ Cells in Lymphocyte of Tumor Stroma.

TABLE 2

Effects of examples on CD4$^+$, CD8$^+$ cells in mice (n = 8)

| Group | CD4$^+$(%) | CD8$^+$(%) |
|---|---|---|
| Normal Group | 45.79 ± 2.89 | 27.37 ± 1.23 |
| Model Group | 12.91 ± 1.14* | 7.34 ± 0.79* |
| Example 1 | 16.89 ± 1.82 | 8.41 ± 0.67 |
| Example 2 | 17.98 ± 2.46$^\#$ | 9.22 ± 0.85 |
| Example 3 | 16.94 ± 5.13 | 9.19 ± 1.02 |
| Example 4 | 17.35 ± 3.02 | 9.35 ± 0.47$^\#$ |
| Example 5 | 26.56 ± 2.41$^\#$ | 14.31 ± 1.04$^\#$ |
| Example 6 | 24.77 ± 2.31$^\#$ | 13.19 ± 1.06$^\#$ |
| Example 7 | 24.23 ± 6.42 | 12.93 ± 2.11$^\#$ |
| Example 8 | 24.89 ± 3.21$^\#$ | 14.12 ± 1.55$^\#$ |

Comment: comparing with the normal group, *P < 0.05; and comparing with the model group, $^\#$P < 0.05.

As shown in Table 2, each of the groups of examples 1 to 8 increased the percentages of CD4$^+$ and CD8$^+$ cells in lymphocyte of tumor stroma in some degree. In addition, the CD4$^+$ and CD8$^+$ differences between examples 5 to 8 and the model group were statistically significant (P<0.05). Therein, detection values of both CD4$^+$ and CD8$^+$ cells in the group of Example 5 were the highest, (26.56±2.41)% and (14.31±1.04)%, respectively. The second was Example 8, with detection values of (24.89±3.21)% and (14.12±1.55)%, respectively. The results indicated that both the individual components and the traditional Chinese medicine compositions increased the percentages of CD4$^+$ and CD8$^+$ cells and improved the immune status of body, which could be used to produce health products and foods for preventing and assisting in treating tumor. However, the effects of the traditional Chinese medicine compositions were better than that of the individual components.

3.3 Effects on Expression Rate of VEGF and TGF-β 1 Positive Cells in Tumor

TABLE 3

Effects of samples on VEGF and TGF-β1 positive cells in tumor

| Group | VEGF (%) | TGF-β 1(%) |
|---|---|---|
| Normal Group | 31.64 ± 3.09 | 35.76 ± 1.21 |
| Model Group | 75.43 ± 9.21* | 70.36 ± 8.25* |
| Example 1 | 70.21 ± 9.11 | 68.25 ± 8.01 |
| Example 2 | 63.95 ± 2.51 | 65.13 ± 0.93 |
| Example 3 | 65.51 ± 5.13 | 66.53 ± 0.95 |
| Example 4 | 66.21 ± 2.95 | 66.65 ± 0.51 |
| Example 5 | 58.53 ± 5.91# | 60.25 ± 3.31# |
| Example 6 | 61.15 ± 2.16# | 61.35 ± 1.35# |
| Example 7 | 61.76 ± 6.31 | 61.74 ± 2.15# |
| Example 8 | 59.31 ± 3.21# | 60.96 ± 1.51# |

Comment: comparing with the normal group, *P < 0.05; and comparing with the model group, #P < 0.05.

As shown in Table 3, each of the groups of examples 1 to 8 decreased the expression rate of VEGF and TGF-β 1 positive cells in mice tumor. Therein, the differences of VEGF and TGF-β 1 positive cells between examples 5 to 8 and the model groups were statistically significant (P<0.05), while the differences between examples 1 to 4 and the model group were not significant. Detection values of both the VEGF and TGF-β 1 positive cells of the group of Example 5 were the least, (58.53±5.91)% and (6.25±$^3$0.31)%, respectively. The second least was Example 8, (59.31±3.21)% and (60.96±1.51)%, respectively. The results indicated that both the individual components and the traditional Chinese medicine compositions decreased the expression rate of VEGF and TGF-β 1 positive cells in mice tumor, inhibited the expression of immune inhibitive factors in local tumor tissue, therefore delaying the development of tumor and improving the immune status of body. They could be used in preparing health products and foods, for preventing and assisting in treating tumor. However, the effects of the traditional Chinese medicine compositions were better than that of the individual components.

It can be concluded from the above results that the traditional Chinese medicine compositions comprising *Lycii fructus* polysaccharide, *Polygonati rhizoma* polysaccharide, *Caryophylli flos* oil and *Cinnamomi cortex* oil can inhibit the growth of tumors, improve percentages of CD4$^+$ and CD8$^+$ cells in the lymphocytes of the tumor stroma, and decrease the expression rate of VEGF and TGF-β 1 positive cells in mice tumor. The role was to inhibit the growth of tumor cells, recover normal immune surveillance and prevent immune escape of the tumor cells. Therein, the traditional Chinese medicine composition which was prepared in Example 6 and consisted of *Lycii fructus* polysaccharide, *Polygonati rhizoma* polysaccharide, *Caryophylli flos* oil and *Cinnamomi cortex* oil has the best effects on assisting in treating tumor and restoring the normal immune surveillance of body, and the effects were better than that of the individual components (P<0.05).

Example 10 Compositions Comprising *Lycii fructus* Polysaccharide, *Polygonati rhizoma* Polysaccharide, *Caryophylli flos* Oil and *Cinnamomi cortex* Oil with Different Ratios, and Effects Thereof

*Lycii fructus* polysaccharide prepared in Example 1, *Polygonati rhizoma* polysaccharide prepared in Example 2, *Caryophylli flos* oil prepared in Example 3 and *Cinnamomi cortex* oil prepared in Example 4 were mixed according to the different weight ratios shown in the Table 4. The compositions were subjected to the test methods of Example 9 for the effects on preventing and/or assisting in treating tumors. The scores of efficacy for restoring normal immune surveillance of the body were obtained (100 point scale, the efficacy for restoring normal immune surveillance by the traditional Chinese medicine composition of Example 5 with a weight ratio of 1:1:1.5:1.5 was recorded as 100 points, and the percentages of other mixing ratios compared to the function test result of Example 5 are recorded as the corresponding scores).

TABLE 4

Compositions comprising LYCII FRUCTUS polysaccharide, POLYGONATI RHIZOMA polysaccharide, CARYOPHYLLI FLOS oil and CINNAMOMI CORTEX oil with different weight ratios, and effects thereof

| | Ratio of Components | | | | | |
|---|---|---|---|---|---|---|
| | 1:5:5:1 | 4:2:5:1 | 2:1:1:2 | 1:2:2:1.5 | 1:1.5:1:1.5 | 1.5:1:1.5:1 |
| Score of Restoring Normal Immune Surveillance | 64 | 75 | 81 | 84 | 92 | 94 |

The results showed that comparing with using the individual components alone, the compositions comprising *Lycii fructus* polysaccharide, *Polygonati rhizoma* polysaccharide, *Caryophylli flos* oil and *Cinnamomi cortex* oil with a mixing ratio of (1~5):(1~5):(1~5):(1~5) showed more significant effects on restoring normal immune surveillance of body. When the mixing ratio was (1~2):(1~2):(1~2):(1~2) the effects were more significant.

Example 11 A Polysaccharide Composition Comprising *Lycii fructus* Polysaccharide and *Polygonati rhizoma* Polysaccharide with a Ratio of 2:2, and Effects Thereof

*Lycii fructus* polysaccharide prepared in Example 1 and *Polygonati rhizoma* polysaccharide prepared in Example 2 were mixed in the best weight ratio of 2:2. The composition was subjected to the test methods of Example 9 for the effects on preventing and/or assisting in treating tumors. The scores of efficacy for restoring normal immune surveillance of the body were obtained (100 point scale, the efficacy for restoring normal immune surveillance by the traditional Chinese medicine composition of Example 5 with a weight ratio of 1:1:1.5:1.5 was recorded as 100 points, and the percentages of other mixing ratios compared to the function test result of Example 5 are recorded as the corresponding scores).

TABLE 5

Compositions comprising LYCII FRUCTUS polysaccharide, POLYGONATI RHIZOMA polysaccharide, CARYOPHYLLI FLOS oil and CINNAMOMI CORTEX oil with different ratios, and effects thereof

| | Ratio of Components | | | | | |
|---|---|---|---|---|---|---|
| | 2:2:0:0 | 1:5:5:1 | 4:2:5:1 | 4:2:2:4 | 2:4:4:3 | 2:3:2:3 | 3:2:3:2 |
| Score of Restoring Normal Immune Surveillance | 46 | 64 | 75 | 81 | 84 | 92 | 94 |

The results showed that comparing with using the polysaccharide composition alone, the compositions comprising *Lycii fructus* polysaccharide, *Polygonati rhizoma* polysaccharide, *Caryophylli flos* oil and *Cinnamomi cortex* oil with a mixing ratio of (1~5):(1~5):(1~5):(1~5) showed more significant effects on restoring normal immune surveillance of body.

Example 12 A Composition Comprising *Caryophylli flos* Oil and *Cinnamomi cortex* Oil with a Ratio of 3:3, and Effects Thereof

*Caryophylli flos* oil prepared in Example 4 and *Cinnamomi cortex* oil prepared in Example 5 were mixed in the best weight ratio of 3:3. The composition was subjected to the test methods of Example 9 for the effects on preventing and/or assisting in treating tumors. The scores of efficacy for restoring normal immune surveillance of the body were obtained (100 point scale, the efficacy for restoring normal immune surveillance by the traditional Chinese medicine composition of Example 5 with a weight ratio of 1:1:1.5:1.5 was recorded as 100 points, and the percentages of other mixing ratios compared to the function test result of Example 5 are recorded as the corresponding scores).

TABLE 6

Compositions comprising LYCII FRUCTUS polysaccharide, POLYGONATI RHIZOMA polysaccharide, CARYOPHYLLI FLOS oil and CINNAMOMI CORTEX oil with different ratios, and effects thereof

| | Ratio of Components | | | | | | |
|---|---|---|---|---|---|---|---|
| | 0:0:3:3 | 1:5:5:1 | 4:2:5:1 | 4:2:2:4 | 2:4:4:3 | 2:3:2:3 | 3:2:3:2 |
| Score of Restoring Normal Immune Surveillance | 42 | 64 | 75 | 81 | 84 | 92 | 94 |

The results showed that comparing with using the oil composition alone, the compositions comprising *Lycii fructus* polysaccharide, *Polygonati rhizoma* polysaccharide, *Caryophylli flos* oil and *Cinnamomi cortex* oil with a mixing ratio of (1~5):(1~5):(1~5):(1~5) showed more significant effects on restoring normal immune surveillance of body.

Example 13 Compositions Comprising *Lycii fructus* Polysaccharide, *Polygonati rhizoma* Polysaccharide, *Caryophylli flos* Oil and *Cinnamomi cortex* Oil with Different Ratios, and Effects Thereof

*Lycii fructus* polysaccharide prepared in Example 1, *Polygonati rhizoma* polysaccharide prepared in Example 2, *Caryophylli flos* oil prepared in Example 3 and *Cinnamomi cortex* oil prepared in Example 4 were mixed according to the weight ratios shown in Table 7 (each composition lacked one or two components). The compositions were subjected to the test methods of Example 9 for the effects on preventing and/or assisting in treating tumors. The scores of efficacy for restoring normal immune surveillance of the body were obtained (100 point scale, the efficacy for restoring normal immune surveillance by the traditional Chinese medicine composition of Example 5 with a weight ratio of 1:1:1.5:1.5 was recorded as 100 points, and the percentages of other mixing ratios compared to the function test result of Example 5 are recorded as the corresponding scores).

TABLE 7

Compositions comprising LYCII FRUCTUS polysaccharide, POLYGONATI RHIZOMA polysaccharide, CARYOPHYLLI FLOS oil and CINNAMOMI CORTEX oil with different ratios, and effects thereof

| | Ratio of Components | | | | | |
|---|---|---|---|---|---|---|
| | 1:5:5:1 | 4:2:5:1 | 4:2:2:4 | 2:4:4:3 | 2:3:2:3 | 3:2:3:2 |
| Score of Restoring Normal Immune Surveillance | 64 | 75 | 81 | 84 | 92 | 94 |

TABLE 7-continued

Compositions comprising LYCII FRUCTUS polysaccharide, POLYGONATI RHIZOMA polysaccharide, CARYOPHYLLI FLOS oil and CINNAMOMI CORTEX oil with different ratios, and effects thereof

| | Ratio of Components | | | | | |
|---|---|---|---|---|---|---|
| | 2:2:0:3 | 2:0:3:3 | 0:3:3:0 | 2:2:3:0 | 0:3:0:3 | 0:2:3:3 |
| Score of Restoring Normal Immune Surveillance | 62 | 61 | 57 | 59 | 54 | 61 |

The results showed that comparing with the compositions that lacked one or two components, the compositions comprising *Lycii fructus* polysaccharide, *Polygonati rhizoma* polysaccharide, *Caryophylli flos* oil and *Cinnamomi cortex* oil with a mixing ratio of (1~5):(1~5):(1~5):(1~5) showed more significant effects on restoring normal immune surveillance of body. When the mixing ratio was (1~2):(1~2):(1~2):(1~2), the effects were more significant.

What is claimed is:

1. A method of inhibiting the growth of tumor, increasing the percentage of $CD_4^+$ and $CD_8^+$ cells in lymphocytes of tumor stroma, decreasing VEGF and TGF-β1 positive cells in tumor tissue, enhancing immunity, preventing and/or assisting in treating tumor, and/or restoring normal immune function, comprising administrating an effective amount of a traditional Chinese medicine composition to a subject in need thereof; wherein the Chinese medicine composition consists of *Lycii fructus* polysaccharide, *Polygonati rhizoma* polysaccharide, *Caryophylli flos* oil and *Cinnamomi cortex* oil; and the weight ratio of *Lycii fructus* polysaccharide, *Polygonati rhizoma* polysaccharide, *Caryophylli flos* oil and *Cinnamomi cortex* oil is (1 to 5):(1 to 5):(1 to 5):(1 to 5).

2. The method according to claim 1, wherein the weight ratio of *Lycii fructus* polysaccharide, *Polygonati rhizoma* polysaccharide, *Caryophylli flos* oil and *Cinnamomi cortex* oil is (1 to 2):(1 to 2):(1 to 2):(1 to 2).

3. The method according to claim 1, wherein the weight ratio of *Lycii fructus* polysaccharide, *Polygonati rhizoma* polysaccharide, *Caryophylli flos* oil and *Cinnamomi cortex* oil is 1:1:1.5: 1.5.

4. The method according to claim 1, wherein the Chinese medicine composition is in the form of a health food or a medicine.

5. The method according to claim 4, wherein the health food or the medicine further comprises a pharmaceutically acceptable excipient or a food acceptable excipient.

* * * * *